(12) United States Patent
Schultz et al.

(10) Patent No.: US 9,995,694 B2
(45) Date of Patent: Jun. 12, 2018

(54) TRAVELING WAVE SPOT PROBE

(71) Applicants: John W. Schultz, Alpharetta, GA (US); Rebecca B. Schultz, Alpharetta, GA (US); James G. Maloney, Marietta, GA (US); Kathleen C. Maloney, Marietta, GA (US)

(72) Inventors: John W. Schultz, Alpharetta, GA (US); Rebecca B. Schultz, Alpharetta, GA (US); James G. Maloney, Marietta, GA (US); Kathleen C. Maloney, Marietta, GA (US)

( * ) Notice: Subject to any disclaimer, the term of this patent is extended or adjusted under 35 U.S.C. 154(b) by 535 days.

(21) Appl. No.: 14/245,178

(22) Filed: Apr. 4, 2014

(65) Prior Publication Data
US 2014/0300373 A1    Oct. 9, 2014

Related U.S. Application Data

(60) Provisional application No. 61/809,356, filed on Apr. 6, 2013.

(51) Int. Cl.
*G01V 3/06* (2006.01)
*G01N 22/00* (2006.01)
(Continued)

(52) U.S. Cl.
CPC .............. *G01N 22/00* (2013.01); *G01R 27/06* (2013.01); *G01R 27/28* (2013.01); *G01R 31/11* (2013.01)

(58) Field of Classification Search
CPC ....... G01F 23/284; G01F 1/667; G01N 22/00; G01N 22/02; G01R 27/28; G01R 27/06; G01R 31/11
(Continued)

(56) References Cited

U.S. PATENT DOCUMENTS 5,337,016 A    8/1994  Wozniak et al.
7,459,916 B2 * 12/2008  Crain ................... G01R 31/001
                                                324/240
(Continued)

OTHER PUBLICATIONS

L. E. R. Petersson et al., "Three-dimensional electromagnetic diffraction of a Gaussian beam by a perfectly conducting half-plane", J. Opt. Soc. Am. A, vol. 19, No. 11, Nov. 2002.
(Continued)

*Primary Examiner* — Jermele M Hollington
*Assistant Examiner* — Raul Rios Russo
(74) *Attorney, Agent, or Firm* — Thomas | Horstemeyer, LLP

(57) ABSTRACT

Various examples of methods and systems are provided for traveling wave spot probes. In one embodiment, among others, a traveling wave spot probe includes one or more antennas positioned proximate to a coated surface. The one or more antennas can be configured to excite a surface traveling wave moving over an area under test by launching radio frequency (RF) energy at approximately a grazing angle to the coated surface under test. The one or more antennas can be positioned on a base placed proximate to the coated surface. The base can define the area of the coated surface under test. In another embodiment, a method for non-destructive testing of a coated surface includes positioning one or more antennas proximate to a coated surface and exciting a surface traveling wave over an area under test by transmitting RF energy via at least a portion of the one or more antennas.

20 Claims, 6 Drawing Sheets

(51) Int. Cl.
 *G01R 27/28* (2006.01)
 *G01R 27/06* (2006.01)
 *G01R 31/11* (2006.01)

(58) Field of Classification Search
 USPC ... 324/76.11–76.83, 459, 600, 629, 637, 642
 See application file for complete search history.

(56) References Cited

U.S. PATENT DOCUMENTS

| | | | | |
|---|---|---|---|---|
| 8,410,805 | B2* | 4/2013 | Uchida | G01R 1/07 324/754.21 |
| 2004/0056803 | A1* | 3/2004 | Soutiaguine | H01Q 9/0414 343/700 MS |
| 2006/0221343 | A1* | 10/2006 | Bouhelier | G01N 21/553 356/445 |
| 2009/0108830 | A1* | 4/2009 | Rose | G01N 27/20 324/71.1 |
| 2011/0117202 | A1* | 5/2011 | Bourke, Jr. | H05B 41/2806 424/490 |
| 2012/0026060 | A1* | 2/2012 | Hanazawa | H01Q 1/2241 343/853 |
| 2012/0274528 | A1* | 11/2012 | Apostolos | H01Q 13/20 343/785 |
| 2013/0266319 | A1* | 10/2013 | Bodan | H01Q 21/068 398/79 |
| 2014/0218049 | A1* | 8/2014 | Sawamoto | G01N 22/04 324/640 |
| 2015/0283392 | A1* | 10/2015 | Bourke, Jr. | H05B 41/2806 604/20 |

OTHER PUBLICATIONS

John W. Schultz, "Near-Field Probe Measurements of Microwave Scattering From Discontinuities in Planar Surfaces", IEEE Transactions on Antennas and Propagation, vol. 51, No. 9, Sep. 2003.

* cited by examiner

TRAVELING WAVE SPOT PROBE

CROSS REFERENCE TO RELATED APPLICATIONS

This application claims priority to U.S. provisional application entitled "Radio Frequency, Traveling Wave Spot Probe" having Ser. No. 61/809,356, filed Apr. 6, 2013, the entirety of which is hereby incorporated by reference.

BACKGROUND

Advanced military vehicles utilize specialty surface coatings to provide electromagnetic attenuation of surface traveling wave phenomena. Specialty surface coatings have thin layers of materials that provide radio frequency (RF) attenuation of surface traveling wave phenomena. These specialty surface coatings are subject to damage as a result of foreign object strikes, thermal stresses, weather erosion, static discharge, and even during routine maintenance activities such as accidental contact with tools or foreign objects. Inspection is performed throughout the life of the vehicle to ensure proper electromagnetic performance of the specialty surface coatings is achieved and maintained.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
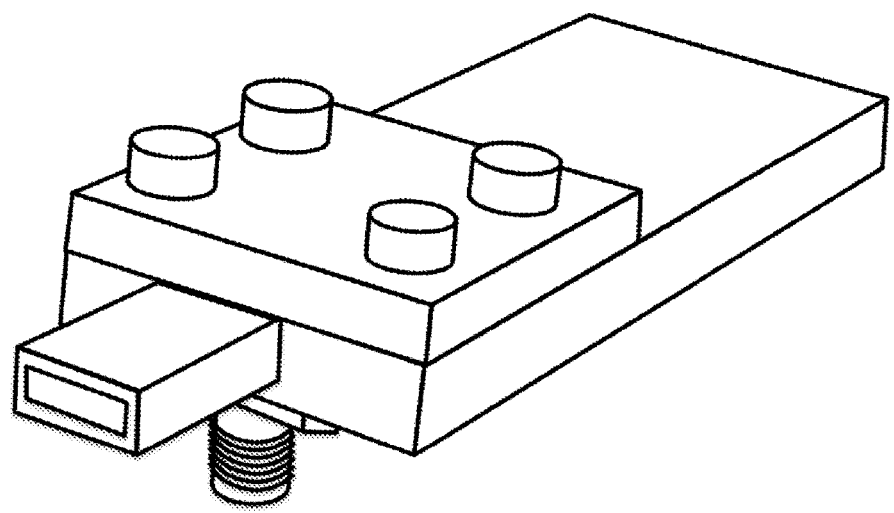
FIG. 1 is an example of a conventional measurement fixture based on an open-ended waveguide probe, which measures reflection, but not travelling wave behavior of a coated surface.

Disclosed herein are various examples related to nondestructive evaluation (NDE) with radio frequency (RF) traveling waves. NDE of specialized coatings can be performed in-situ using a spot probe. Reference will now be made in detail to the description of the embodiments as illustrated in the drawings, wherein like reference numbers indicate like parts throughout the several views.

When damage compromises specialty surface coatings, the damage can be characterized electromagnetically to assess the impact to vehicle performance and to determine the proper course of repair. Inspection of a specialty surface coating ensures that proper electromagnetic performance is achieved and maintained. A spot probe can be used for in-situ testing of the electromagnetic performance of a coating. It is desirable that the spot probe device be nondestructive, as well as portable and capable of measuring coatings on both flat and curved surfaces.

Local electromagnetic performance of a specialty coating can be determined using a waveguide reflectometer (or resonant probe) consisting of an open-ended waveguide that can form a resonant cavity with the surface under test. Referring to FIG. 1, shown is an example of a rectangular, near field, waveguide probe with an open end that can be placed in close proximity to the surface under test to strongly interact with materials on the surface. The waveguide reflectometer indicates the normal-incidence reflectivity of the surface under test but does not provide any information on grazing angle performance or surface traveling wave performance. However, the waveguide reflectometer can be inaccurate when the coating is on a curved surface. Additionally, the waveguide reflectometer is not particularly sensitive to coating defects, which have a higher importance at grazing angles.

The measurement of grazing angle electromagnetic performance can be an important driver for determining how strongly a structure scatters incident electromagnetic energy. At grazing incidence, the propagating electromagnetic energy is called a surface wave or a travelling wave, and includes energy propagating parallel or grazing to the plane of the surface. This is in contrast with the phenomena of specular reflection, where the energy is incident at some other angle besides grazing, and the surface reflects the incident energy into a complimentary angle determined by Snell's law. On a vehicle, traveling waves occur when incident radar energy interacts with a discontinuity in the surface such as leading or trailing edge. In this case, the scatter from that discontinuity launches a surface traveling wave that follows the surface of the vehicle until it encounters another discontinuity such as a gap or another edge. At that point, the surface traveling wave scatters and radiates out, away from the vehicle. A specialty surface coating is used to attenuate this traveling wave phenomenon, so that it is dissipated before it encounters other discontinuities and scatters. Similarly an antenna mounted on a surface can launch traveling waves that interfere with another antenna located on the same surface. In this case, a specialty surface coating attenuates the interfering signal between the two antennas.

A traveling wave table can be used to measure grazing angle or surface wave performance of coating materials. The traveling wave table includes a flat or gently curved metal surface with a source antenna at one location and a receive antenna at a second location. To test a coating material, it is placed between the source antenna and the receive antenna, and the relative attenuation of the surface wave by the material is determined by measuring the insertion loss between the two antennas. Calibration is normally performed by measuring the traveling wave transmission on the traveling wave table without any treatment applied.

Since the antennas of the traveling wave table are electrically small, the radiation from them is point-source-like. When a material is placed between the source and receive antennas, the material can act as a waveguide or lens. This can artificially focus the traveling wave so that the measured insertion loss due to the coating material is less than that for a more realistic plane wave source. The traveling wave table is also not particularly portable. In particular, an extracted material specimen is placed on the fixture for measurement and testing.

An RF traveling wave (TW) spot probe (or TWSP) can be used to directly measure attenuation of a locally excited surface traveling wave. The RF traveling wave spot probe can be small and portable to provide non-destructive testing of a coating material in-situ on a vehicle. The RF TWSP includes two or more linear antenna arrays in a compact frame that allows them to be positioned adjacent to the surface to be measured. The antennas transmit and receive a surface traveling wave over a confined area of the surface under test.

Figure 2A:
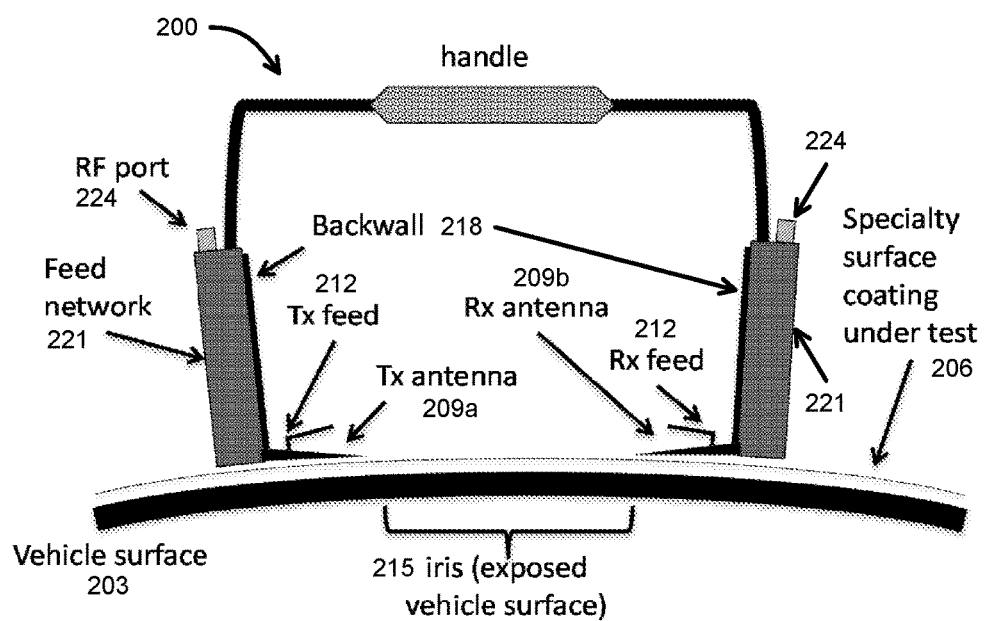
FIGS. 2A and 2B are explanatory diagrams showing an example of a traveling wave (TW) spot probe from side and top perspectives, respectively, in accordance with various embodiments of the present disclosure.
Figure 2B:
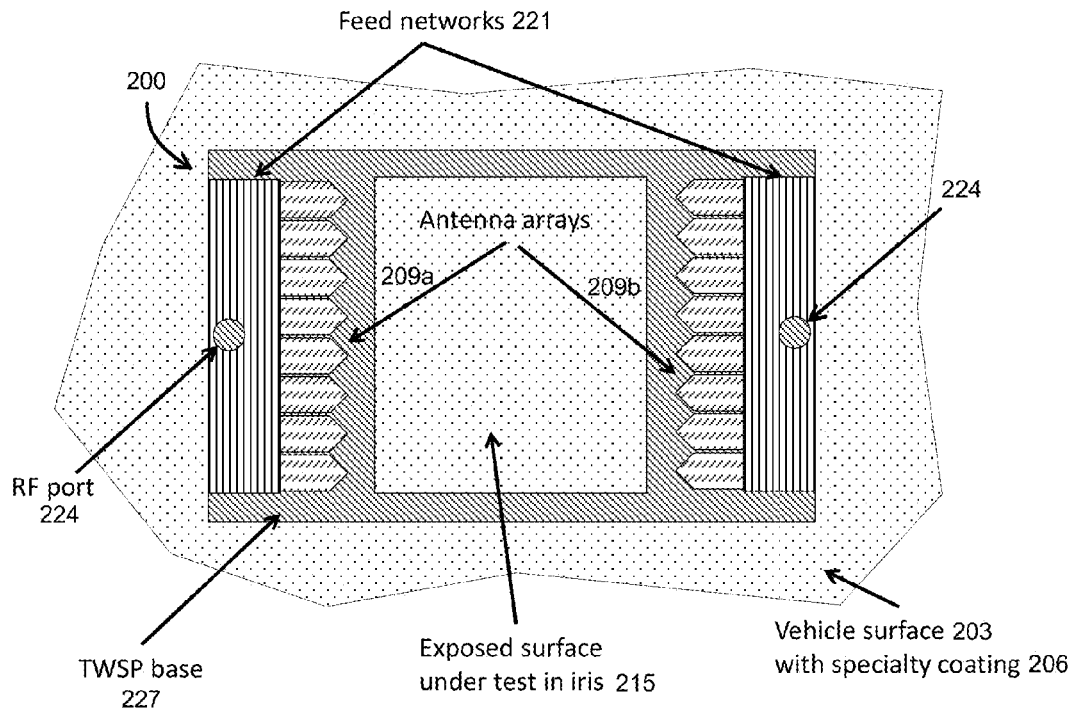
Figure 3:
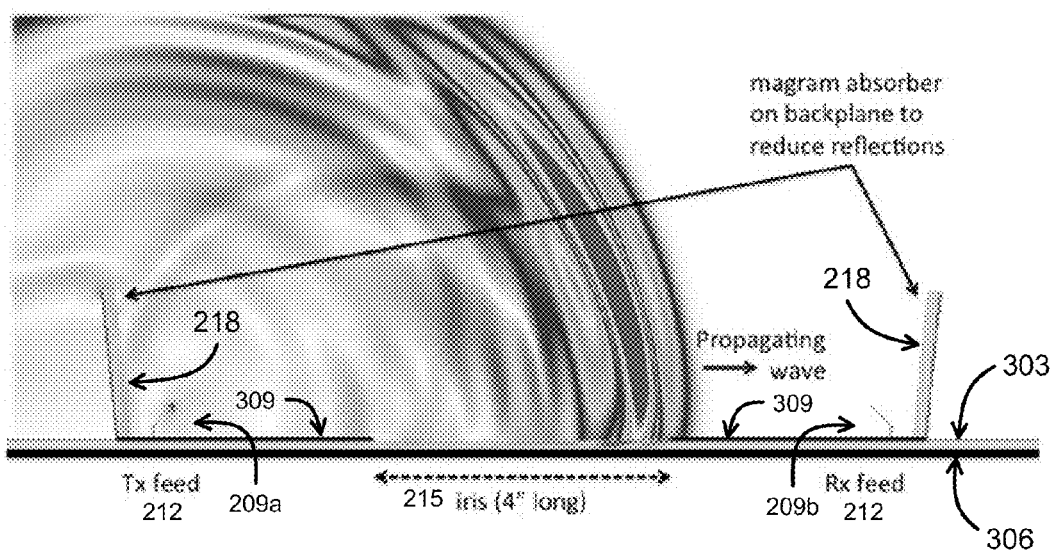
FIG. 3 is a computer-simulated representation of electric fields of a traveling wave of the TW spot probe of FIGS. 2A and 2B, in accordance with the various embodiments of the present disclosure.

Referring to FIGS. 2A and 2B, shown are side and top cross-sectional views, respectively, of an example of a TW spot probe 200 for testing a vehicle surface 203 with a surface coating 206. Vehicles can include, but are not limited to, aircraft, ships, boats, and/or land vehicles (e.g., cars, trucks, tanks, etc.). The TW spot probe 200 includes a pair of linear arrays of monopole antennas 209 on either side of an illumination area (defined by an iris 212) to be interrogated. As illustrated in FIG. 2B, the pair of linear arrays of monopole antennas 209 are substantially parallel. The first linear array of monopole antennas 209a generates a surface wave and the second linear array of monopole antennas 209b receives the surface wave after it has propagated over the area to be evaluated (e.g., a small region of a vehicle surface). The antenna design for both receive (Rx) and transmit (Tx) functions may use a linear array of monopole feeds 212 that provide plane-wave-like traveling wave excitation. The monopole feeds 212 can be optimized for the operating conditions of the TW spot probe 200. FIG. 3 shows a simulation result illustrating the e-fields as a traveling wave propagates across an iris 215 between Tx and Rx antennas 209. Transmission power of the traveling wave can be adjusted for testing at various energy levels. For example, the power level may be adjusted to simulate RF levels expected to be encountered by the surface coating during operation of the vehicle. In other cases, the power level may be increased to a higher level for identification of faults or defects in the coating or structure.

As shown in the example of FIGS. 2A and 2B, each feed array may be backed by a vertically oriented conductive backplane (or backwall) 218 to ensure that traveling wave propagation only goes in one direction: from the Tx antenna 209a to the Rx antenna 209b, and therefore reduces or minimizes unwanted interaction with other nearby structures or materials in proximity to the measurement area. FIG. 2A shows the backwall 218 tipped outward away from the antennas at an angle greater than 90 degrees, to minimize multipath reflections within the probe. When the antennas are linear arrays, then a feed network or power combiner 221 may be used to distribute energy transmitted to a single port 224 into each of the elements 209a in the Tx antenna array, or to combine energy from each of the elements 209b in the Rx antenna array into a single port 224 for reception. The feed network 221 may be a separate unit from the array of antennas 209, or may be directly integrated into the array of antennas 209.

The Tx and Rx feeds 212 are mounted on a base 227 of the TW spot probe 200, which can include a metal sheet that contains an iris 215. The TWSP base 227 can be tapered in thickness or canted downwards from the backplane 218 to an edge at the iris 215 as shown in FIG. 2A, so that the iris edge is in close proximity to the surface under test. The iris 215 is where the propagating wave directly interacts with the coated surface of the vehicle. The iris 215 also ensures that the measured performance is only of the exposed spot and is not influenced by materials and/or structures in the surrounding area. In actual use, sequential measurements can be obtained by sequentially moving or sliding the TW spot probe 200 across the surface of the vehicle. An image or plot can be constructed from the measurements showing the traveling wave absorption as a function of the position on the vehicle. Another advantage of the iris 215 is that testing can be performed if the edge of the iris 215 is in close proximity to the vehicle surface, rather than needing the whole bottom surface of the TWSP base 227 to be on the surface. Thus, a slight convex or concave curvature is as easily measured as a flat surface, since the region within the iris 215 does not have to be exactly coplanar with the bottom of the TW spot probe 200. For example, a 50 inch radius of curvature can be examined with an iris 215 that is 6 inches or smaller.

The probe geometry shown in FIGS. 2A and 2B is designed for hand-held use, and is compact and lightweight. For example, the width of the TW spot probe 200 in FIG. 2A may be 10 inches or less. It may also be possible to have it mounted onto an automated positioning system, such as an industrial robot for use as a quality assurance measurement device in a factory setting. In alternative embodiments, the position of the TW spot probe 200 may be monitored using, e.g., a wireless tracking system. In some implementations, the TW spot probe 200 may receive signals that can be used to determine the position of the TW spot probe 200. In other implementations, the TW spot probe 200 may transmit a signal that can be used to determine the position of the TW spot probe 200 by an external unit. Signals may be provided to indicate when a measurement is being taken by the TW spot probe 200.

The TW spot probe 200 is used with a microwave source and receiver such as a network analyzer, which can operate over a range from about 2 GHz to about 20 GHz. Other frequency ranges may also be possible such as, e.g., millimeter waves (>20 GHz) or UHF/VHF (<2 GHz). The TW spot probe 200 may be tethered to an external network analyzer by a flexible cable coupled to one or more RF ports 224. In this case, the analyzer can sit on a separate cart or be carried in a backpack or a fanny pack worn by an operator. In some implementations, the microwave source and receiver and the TW spot probe 200 may be integrated as a single unit, which has the added benefit of eliminating phase variations that occur with cable flexure. A power source such as, e.g., a battery can also be included in the TW spot probe 200. The TW spot probe 200 can also include a communication interface that allows for wireless communication (e.g., Bluetooth, WiFi, etc.) with an external analyzer or other computing device for storage and/or analysis of the captured measurement data.

To demonstrate the operation of the spot probe 209, simulations were run with finite difference time domain (FDTD) simulation code. FDTD works by inserting fields into a simulation space and then marches through time, calculating the electric and magnetic fields within the simulation space at each instant in time. Referring to FIG. 3, shown is an example of one instant in time of the simulation, where the wave front radiated by a Tx antenna 209a has traveled from left to right on the surface of the vehicle (bottom of the image) and has just passed over a four inch iris 212.

A surface coating 206 (FIG. 2A) as modeled using a 120 mil thick, commercially available magnetic absorber 303 having carbonyl iron powder (CIP) in a polyurethane matrix to reduce reflections. Measured permittivity and permeability data were input into a dispersive material model within the FDTD simulation to fully account for the frequency dependent properties. The absorber 303 was backed by a metal ground plane 306 to simulate the surface 203 (FIG. 2A) of a vehicle.

Backplanes 218 are also placed behind each antenna 209 to minimize back lobe radiation. The backplanes 218 can also be lined with absorber for the purposes of minimizing multi-path reflections. A thin metal sheet 309 was integrated at the bottom of the TW spot probe 200, which rests on top of the absorber coating 303 of the vehicle. The iris 215 in this sheet was placed mid-way between the Tx and Rx feeds 212. Because simple monopoles are somewhat narrow-band, the feed monopoles in this simulation were diamond shaped (and canted) to improve the bandwidth (which would be analogous to a bow-tie antenna) so that a range from about 2 GHz to about 20 GHz band could be sampled.

Figure 4:
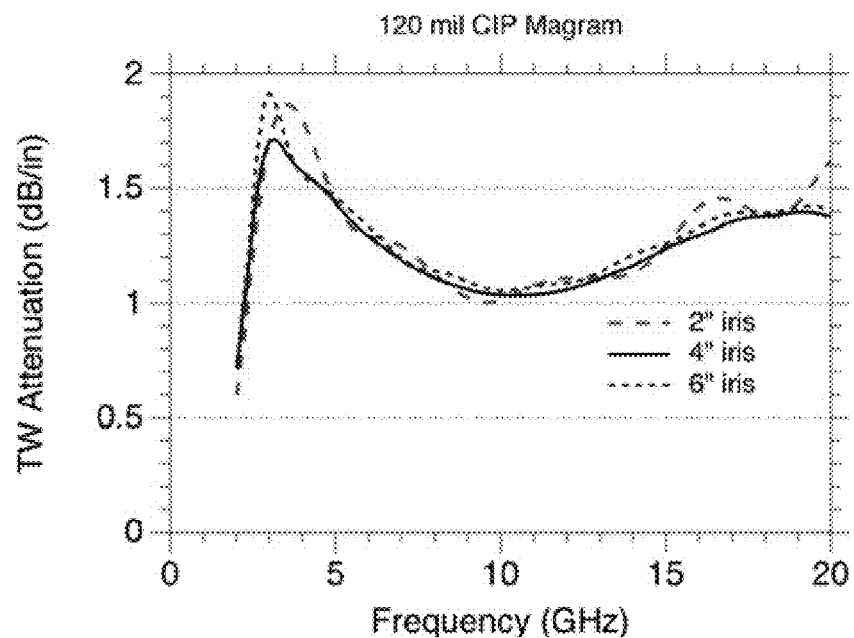
FIG. 4 shows an example of simulated traveling wave attenuation for various iris lengths of the TW spot probe of FIGS. 2A and 2B, in accordance with the various embodiments of the present disclosure.

Using the simulation with a 4 inch iris 215, along with simulations for 2 inch and 6 inch irises 215, the insertion loss data of the virtual coating were determined. Normalizing the simulated insertion loss data by the total length of the iris 215 provides a direct measurement of the traveling wave absorption in dB per inch. FIG. 4 shows a plot of traveling wave (TW) attenuation of the simulation data against transmission frequency. Because of the iris length normalization, the dB/inch loss data should be identical independent of the iris size, as shown in FIG. 4. A couple of other interesting effects are also evident in the plots of FIG. 4. For example, the 2-inch iris data exhibited more ripple than the 4 inch or 6 inch iris 215. This may be caused by poorer sensitivity due to the shortened interaction area of the traveling wave with the absorbing coating. This may be improved by either increasing the size of the iris 215 and/or by improving the efficiency of the monopole feeds 212.

The attenuation performance of the CIP absorber 303 also drops off dramatically below about 3 GHz in these simulations. This is a real material coating effect due to the combination of two factors. First, the imaginary part of the magnetic permeability (the loss factor) of CIP materials drops off below these frequencies so that the magnetic absorbent material becomes a significantly less capable absorber. Second, the fixed thickness of the absorber 303 (120 mils) becomes much smaller than a wavelength as frequency decreases. The combination of these two characteristics means that this simulated material becomes ineffective as a traveling wave absorber at frequencies below a couple of GHz. The simulations confirmed this expected behavior.

Another interesting behavior that is evident in the plots of FIG. 4 is that the attenuation performance above 3 GHz is not a simple monotonic increase with frequency, but instead exhibits a non-trivial frequency behavior. This can be due to the fact that a magneto-dielectric coating on a metal ground plane behaves like a lossy waveguide. As the frequency increases, additional higher-order waveguide modes are present. Some of these modes couple more strongly into loss than others. Thus, the frequency dependent behavior shown in FIG. 4 can be a function of the allowed waveguide modes at each given frequency and is expected. The number of allowed waveguide modes at any given frequency depends on both the thickness and the frequency dependent permittivity and permeability.

Possible modes of operation for the TW spot probe 200 include an insertion loss mode and a scatter mode. When in the insertion loss mode, the attenuation of a surface traveling wave on the surface under test is determined. The scatter mode measures the presence of defects on, in, or under a coating on a conductive surface.

During the insertion loss mode, the microwave transmitter sends energy to a Tx antenna 209a, where the energy is emitted by the Tx antenna 209a and travels across the exposed surface under test. The transmitted energy is then received by an Rx antenna 209b on the opposite side of the exposed surface under test. A calibrated insertion loss can be determined as the ratio of the insertion loss received with the surface under test to an insertion loss received with no surface coating, which was previously measured for an untreated surface. Surface wave attenuation can be calculated in dB per unit length by dividing the calibrated insertion loss by the total length of the iris 215 (FIG. 2A), or the exposed surface, in the direction of travel. In the following examples, the unit length is expressed in inches; however metric units or wavelength normalized units may also be used.

Figure 5:
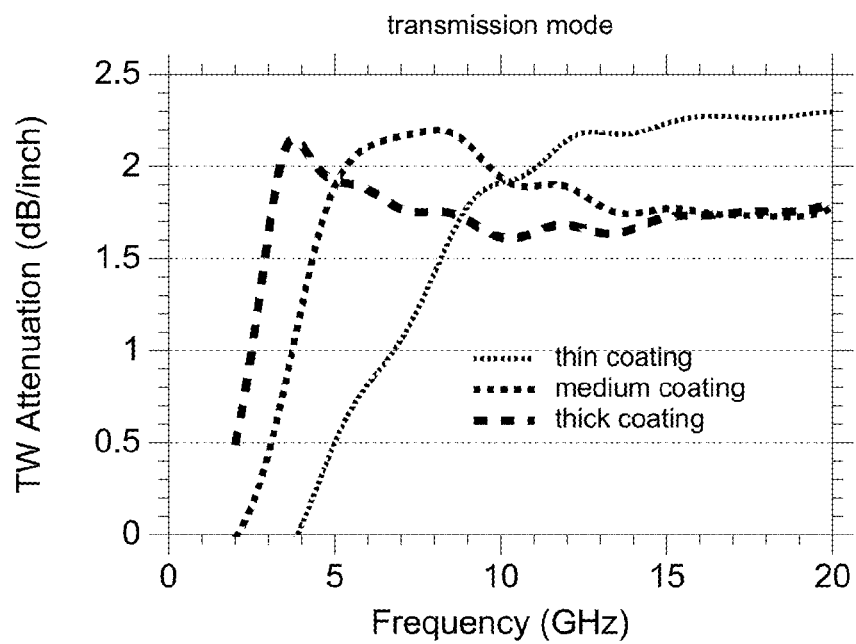
FIG. 5 shows an example of measured traveling wave attenuation for different thickness coatings on a conductive ground plane using the TW spot probe of FIGS. 2A and 2B, in accordance with the various embodiments of the present disclosure.

Referring to FIG. 5, shown is a plot of examples of measured surface wave attenuation in dB/inch for three different surface coatings. These data were obtained with a TW spot probe 200 having a 6 inch wide iris 215 and 8-element linear array antennas 209 on opposite sides of the 6 inch iris 215. In this example, the antenna arrays 209 had a useful performance from about 2 GHz to about 20 GHz. Additional processing of the measured data was also used, which included time domain gating. Time domain gating can be used in materials measurement fixtures to minimize multipath reflections that add measurement error. The data shown in FIG. 5 was transformed from the frequency domain into the time domain via a Fourier Transform for filtering. A window function was convolved with the measured signal to only retain data near the time of interest. For the data shown in FIG. 4, a 1-nanosecond wide window was used. An inverse Fourier Transform is then used to convert the processed data back into frequency domain.

The measured surface treatments indicated in FIG. 4 consisted of three different thicknesses of absorber material 303 (FIG. 3) placed adjacent to the conductive surface 306 (FIG. 3). As the data show, the TW spot probe 200 is able to determine the traveling wave attenuation, and to discern between absorber coatings of different thicknesses. The thick coating was approximately 0.090 inch thick, the medium coating was approximately 0.060 inch thick and the thin coating was approximately 0.030 inch thick. The TW spot probe 200 can receive energy over a wide bandwidth of frequencies, enabling the determination of spectral signature of the surface wave attenuation. For example, if only data at 10 GHz were obtained, FIG. 4 shows that it would be impossible to uniquely determine the thickness of the coating. However, by observing data across a wider bandwidth of frequencies, a unique signature as a function of coating thickness (or other properties) can be identified, better enabling the operator to determine the physical makeup of the coating under test. A series of measurements may be taken as the transmission frequency is varied over a defined range. While the example of FIG. 4 illustrates single layer coatings, the TW spot probe 200 can also be used to evaluate more complex, multi-layer coatings.

As previously noted, the TW spot probe 200 can also operate in scatter mode, were the TW spot probe 200 is used to measure small levels of electromagnetic scatter from a defect in a coated surface. For the probe geometry illustrated in FIG. 2A, the scattering mode uses only one of the two antennas 209, and that antenna 209 is used to both illuminate the area under test and to receive the backscattered electromagnetic energy from a defect present within that area.

The calibration method for backscatter is somewhat different than the travelling wave attenuation. Backscatter uses both a reflection standard and a matched load (or isolation) standard, since the reflection from the TW spot probe 200 itself must be vector-subtracted out to obtain a reasonable signal to noise measurement. The reflection standard may be a flat metal sheet placed vertically on the horizontal metal surface and in between the two antennas 209 of the TW spot probe 200 (e.g., in the iris 215 of FIG. 2B). The isolation standard is simply the response of the TW spot probe 200 on an ideal horizontal metal plate with nothing placed in the measurement region (or iris 215).

The calibrated scatter can then be calculated by first subtracting the isolation data from both the response data with the reflection standard in position and the measurement of the surface under test. Once this is done, the ratio of the isolation-subtracted surface under test data to the reflection standard response data then provides the calibrated scatter.

Figure 6A:
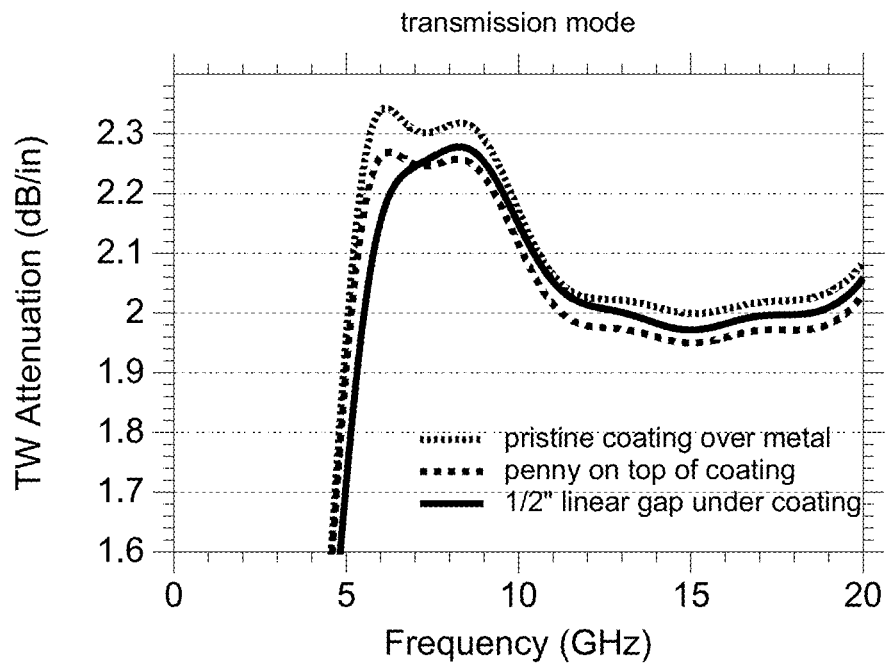
FIG. 6A shows an example of measured traveling wave attenuation as a function of frequency for a coating with various defects using the TW spot probe of FIGS. 2A and 2B, in accordance with the various embodiments of the present disclosure.
Figure 6B:
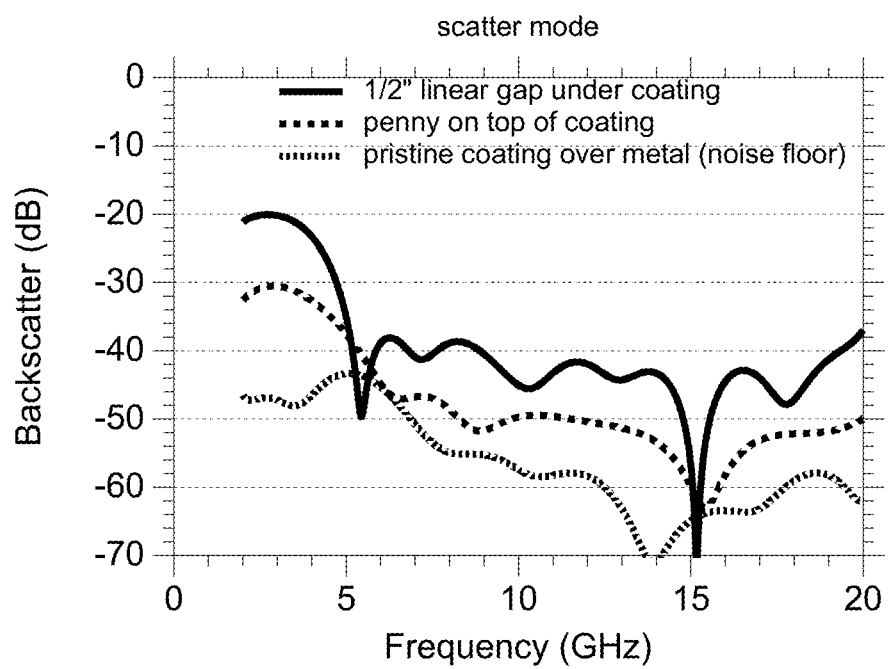
FIG. 6B shows an example of measured traveling wave backscatter as a function of frequency for a coating with various defects, in accordance with the various embodiments of the present disclosure.

An example of insertion loss and backscatter results measured by the same TW spot probe 200 is shown in FIGS. 6A and 6B, respectively. Plots of the measured data include measurements with a small metal defect (e.g., a penny) placed on top of a 0.060 inch thick coated surface, as well as measurements with a 0.5 inch gap in the conductive ground plane underneath the 0.060 inch coating. Also shown in FIGS. 6A and 6B are measurements with the ideal case of the 0.060 inch thick coating on a pristine metal sheet or ground plane. The insertion loss data of FIG. 6A show negligible differences between the three measurements, while the backscatter data of FIG. 6B show easily detectable differences between the defect-free case and the other two defect examples. In particular, the presence of defects raises the level of scatter measured by the device.

Figure 7:
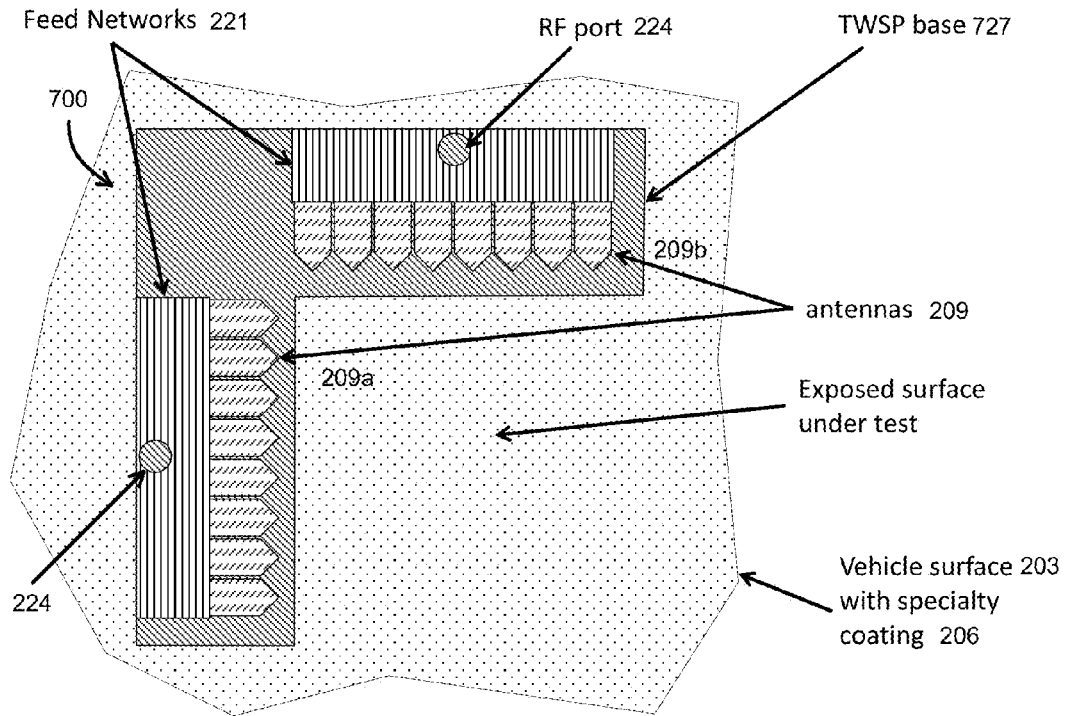
FIG. 7 is an explanatory diagram showing an example of a TW spot probe suitable for bistatic measurement of traveling wave scatter, from a top perspective, in accordance with various embodiments of the present disclosure.

While the example of FIG. 6B shows scatter measured in the backwards direction (monostatic), it is also possible to use a traveling wave spot probe to measure scatter in other directions (bistatic). For this, the antennas 209 of the TW spot probe 700 can be substantially perpendicular to each other as shown in FIG. 7. In the bistatic configuration, one array of Tx antennas 209a illuminates a region under test, while a second array of Rx antennas 209b is used to receive the energy scattered to the side. The arrangement of the antennas 209 can be reversed with antennas 209b illuminating the region under test and antennas 209a receiving the scattered energy. While the TWSP base 727 is open and does not include an iris as in FIGS. 2A and 2B, the TWSP base 227 can be tapered from the backplane 218 to an edge of the base 227. The advantage of this configuration over the monostatic case of FIGS. 2A and 2B is that the use of separate transmit and receive arrays can be more accurate since it reduces the voltage standing wave ratio (VSWR) effects from the antennas 209 in the measured signal. The antennas 209 can be resistively loaded to improve VSWR and/or reduce or minimize multipath reflections.

Figure 8:
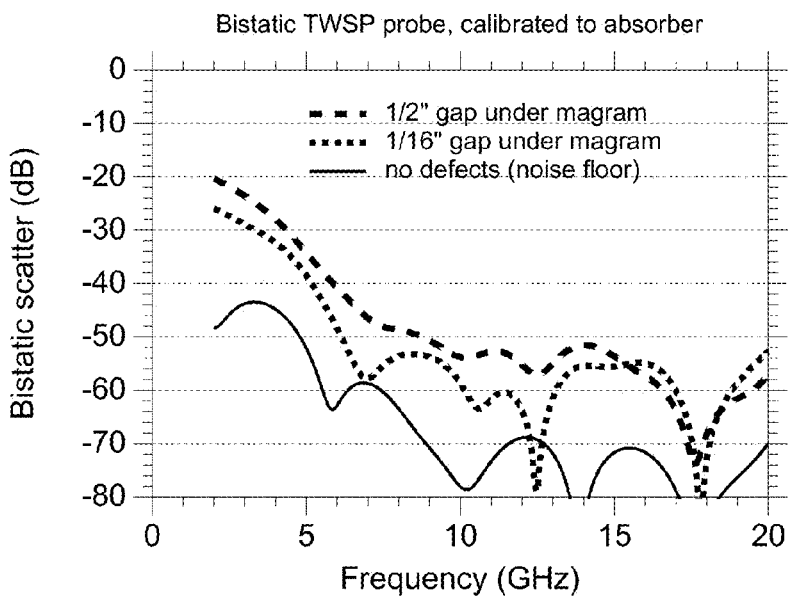
FIG. 8 shows an example of measured bistatic traveling wave scatter for a coating with various defects underneath using the TW spot probe of FIG. 7, in accordance with various embodiments of the present disclosure.

Examples of measured bistatic scatter with the TW spot probe 700 geometry of FIG. 7 are shown in FIG. 8. Plots of the measured data include measurements with a 0.5 inch gap and a 0.125 inch gap in the conductive ground plane underneath the magnetic absorbent coating. Also shown in FIG. 8 are measurements for the ideal case (or noise floor) with no defects in the ground plane. The data were obtained with a TW spot probe 700 having 8-element linear array antennas 209 substantially perpendicular to each other. In this example, the antenna arrays 209 obtained measurements in a range from about 2 GHz to about 20 GHz. As can be seen in FIG. 8, the shape and amplitude of the bistatic scatter plots change with variations in the gap distance under the absorbent coating.

Figure 9:
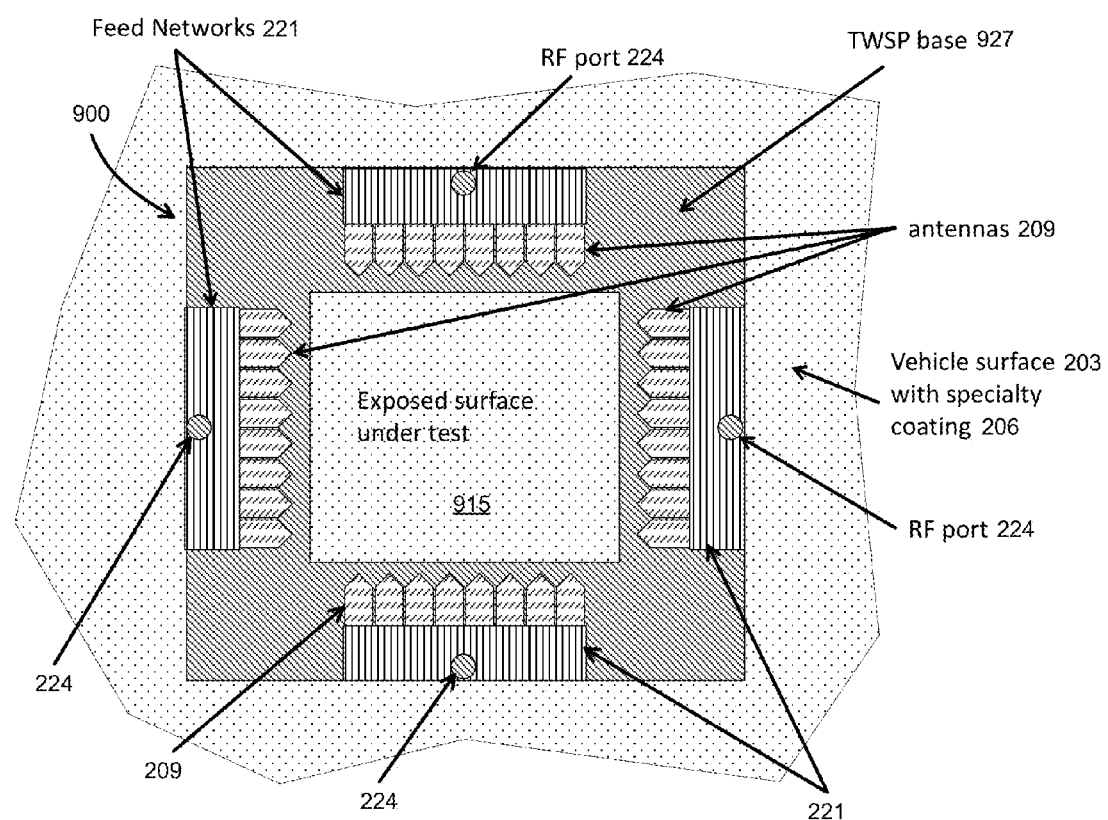
FIG. 9 is an explanatory diagram showing an example of a TW spot probe suitable for bistatic and monostatic measurement of traveling wave scatter, from a top perspective, in accordance with various embodiments of the present disclosure.

Referring to FIG. 9, shown is a TW spot probe 900 configured to measure both bistatic and monostatic scatter, along with traveling wave attenuation. In the example of FIG. 9, the TW spot probe 900 includes a plurality of arrays of antennas 209, where each array of antennas 209 is substantially perpendicular to the adjacent arrays of antennas 209. In the example of FIG. 9, four arrays of antennas 209 are configured in a square. The TWSP base 927 surrounds a rectangular iris 915 defining the exposed surface under test. The cross-sectional view of FIG. 2A can also be applied to the TW spot probe 900 of FIG. 9. The configuration allows the TW spot probe 900 to perform measurements for insertion loss, monostatic scatter and bistatic scatter by controlling transmission and reception by the various arrays of antennas 209 as previously described.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A traveling wave spot probe, comprising:
   a base that rests on a coated surface, the base defining an area of the coated surface under test, the base repositionable on the coated surface; and
   one or more antennas positioned on the base, the one or more antennas configured to excite a surface traveling wave moving over the area of the coated surface under test by launching radio frequency (RF) energy at approximately a grazing angle to the coated surface under test.

2. The traveling wave spot probe of claim 1, wherein a first antenna of the one or more antennas transmits the surface traveling wave and a second antenna of the one or more antennas receives an attenuated surface traveling wave.

3. The traveling wave spot probe of claim 1, wherein the one or more antennas comprise a linear array of antennas.

4. The traveling wave spot probe of claim 3, wherein the one or more antennas comprise a plurality of linear arrays of antennas.

5. The traveling wave spot probe of claim 4, wherein a first linear array of the plurality of linear arrays of antennas is substantially perpendicular to a second linear array of the plurality of linear arrays of antennas.

6. The traveling wave spot probe of claim 3, further comprising a feed network configured to distribute RF energy to each element of the linear array of antennas to excite the surface traveling wave.

7. The traveling wave spot probe of claim 6, wherein an external network analyzer is coupled to the feed network via an input port.

8. The traveling wave spot probe of claim 1, further comprising a microwave transmitter and a microwave receiver communicatively coupled to the one or more antennas.

9. The traveling wave spot probe of claim 8, wherein the microwave transmitter is configured to provide RF energy to excite the surface traveling wave in a range from about 2 GHz to about 20 GHz.

10. The traveling wave spot probe of claim 1, wherein the base comprises an iris defining the area of the coated surface under test.

11. The traveling wave spot probe of claim 1, wherein the coated surface under test is a curved surface.

12. The traveling wave spot probe of claim 1, wherein the one or more antennas transmits the surface traveling wave and the one or more antennas receives monostatic backscatter from the coated surface under test.

13. The traveling wave spot probe of claim 1, wherein a first antenna of the one or more antennas transmits the surface traveling wave and a second antenna of the one or more antennas receives bistatic backscatter from the coated surface under test.

14. The traveling wave spot probe of claim 13, wherein the first antenna of the one or more antennas receives monostatic backscatter from the coated surface under test.

15. The traveling wave spot probe of claim 1, wherein the one or more antennas are resistively loaded to improve VSWR or reduce multipath reflections.

16. The traveling wave spot probe of claim 1, wherein the traveling wave spot probe is a hand-held configuration that provides in-situ non-destructive evaluation of a larger body comprising the coated surface.

17. The traveling wave spot probe of claim 16, wherein the larger body is an aircraft, ship or land vehicle including the coated surface under test.

18. A method for non-destructive testing of a coated surface, comprising:
   positioning a base of a traveling wave spot probe on the coated surface, the base defining an area of the coated surface under test, where the traveling wave spot probe includes one or more antennas positioned on the base proximate to the coated surface; and
   exciting a surface traveling wave over the area of the coated surface under test by transmitting radio frequency (RF) energy via at least a portion of the one or more antennas, the RF energy launched at approximately a grazing angle to the coated surface under test.

19. The method of claim 18, further comprising receiving an attenuated surface traveling wave or bistatic backscatter via at least another portion of the one or more antennas.

20. The method of claim 18, further comprising receiving monostatic backscatter via the at least a portion of the one or more antennas.

* * * * *